United States Patent
Kay et al.

(10) Patent No.: US 6,887,492 B2
(45) Date of Patent: May 3, 2005

(54) MAGNESIUM PLUS INTERACTIVE AGENT DELIVERY

(75) Inventors: Robert A. Kay, LaMirada, CA (US); Larry K. Thomas, Irvine, CA (US)

(73) Assignee: Leiner Health Services Corp., Carson, CA (US)

( * ) Notice: Subject to any disclaimer, the term of this patent is extended or adjusted under 35 U.S.C. 154(b) by 132 days.

(21) Appl. No.: 10/017,478

(22) Filed: Dec. 14, 2001

(65) Prior Publication Data

US 2003/0129228 A1 Jul. 10, 2003

(Under 37 CFR 1.47)

Related U.S. Application Data

(60) Provisional application No. 60/255,616, filed on Dec. 14, 2000.

(51) Int. Cl.[7] .............................. A61K 9/28; A61K 9/20; A61K 9/22; A61K 9/48; A61K 9/24
(52) U.S. Cl. ...................... 424/474; 424/464; 424/468; 424/463; 424/451; 424/457; 424/472
(58) Field of Search ................................ 424/474, 464, 424/468, 463, 451, 457, 472, 469, 489

(56) References Cited

U.S. PATENT DOCUMENTS

| | | | |
|---|---|---|---|
| 4,104,370 A | 8/1978 | Bloch | |
| 4,339,428 A | * 7/1982 | Tencza | |
| 4,415,547 A | 11/1983 | Yu et al. | |
| 4,752,479 A | 6/1988 | Briggs et al. | |
| 4,761,274 A | 8/1988 | Denick, Jr. et al. | |
| 4,954,349 A | 9/1990 | Sheth et al. | |
| 4,965,072 A | 10/1990 | Alexander et al. | |
| 5,002,774 A | 3/1991 | Agrawala et al. | |
| 5,073,377 A | 12/1991 | Alexander et al. | |
| 5,089,276 A | 2/1992 | Yamashita et al. | |
| RE34,222 E | 4/1993 | Bloch | |
| 5,219,889 A | 6/1993 | Walsdorf et al. | |
| 5,401,512 A | 3/1995 | Rhodes et al. | |
| 5,476,652 A | 12/1995 | Chinuki et al. | |
| 5,762,962 A | 6/1998 | Georgiades et al. | |
| 5,811,126 A | * 9/1998 | Krishnamurthy | |
| 5,849,338 A | 12/1998 | Richardson et al. | |
| 5,858,412 A | 1/1999 | Staniforth et al. | |
| 5,914,132 A | 6/1999 | Kelm et al. | |
| 6,020,002 A | 2/2000 | Myers et al. | |
| 6,042,849 A | * 3/2000 | Richardson et al. | |
| 6,258,846 B1 | * 7/2001 | Hermelin et al. | |

FOREIGN PATENT DOCUMENTS

WO 92/22305 12/1992

* cited by examiner

Primary Examiner—Thurman K. Page
Assistant Examiner—Humera N. Sheikh
(74) Attorney, Agent, or Firm—Hoffmann & Baron, LLP

(57) ABSTRACT

The present invention is an orally administered pharmaceutical composition that provides for the controlled release of magnesium. The composition has an interactive agent component and a magnesium component which has an enteric coating that controls the release of the magnesium until the composition is in the small intestine or colon. The other component is released in the stomach and is substantially absorbed prior to the release of the magnesium component. Normally, the interactive agent component decreases the absorption of magnesium when the two components are released simultaneously in the gastrointestinal tract.

14 Claims, 1 Drawing Sheet

MAGNESIUM PLUS INTERACTIVE AGENT DELIVERY

This application claims the benefit of U.S. Provisional Application No. 60/255,616, filed on Dec. 14, 2000.

BACKGROUND OF INVENTION

The present invention relates to the delivery of magnesium and an additional interactive agent to a host while minimizing unwanted interaction between magnesium and the agent.

Magnesium is an important constituent of all soft tissues and bones. It also assists in hundreds of enzyme reactions essential to body functions. Magnesium has been found to suppress nervousness and tremors. Magnesium serves several functions when a human or animal ingests it. Studies have reported that magnesium helps convert carbohydrates, protein, and fat into energy; regulates muscle contraction, nerve transmission, and bone formation; regulates heartbeat; and may prevent kidney stones. The best food sources of magnesium include legumes, nuts, soybeans, dark green leafy vegetables, whole grain breads and cereals, seafood, meats, milk, and other dairy products. The recommended daily requirement of magnesium in the diet of human beings is between 280 and 350 mg per day, although some studies have shown a daily requirement of as much as 500 mg per day or more, depending on the body weight of the individual.

Magnesium derives its name from magnesite, a magnesium carbonate mineral, and this mineral in turn is said to owe its name to magnesite deposits found in Magnesia, a district in the ancient Greek region of Thessaly. In many parts of the world, continuous farming of land has resulted in the depletion of magnesium in soils. Magnesium has been further depleted in plants by the use of potassium and phosphorus laden fertilizers which alter the plant's ability to uptake magnesium. Water from deep wells contains magnesium and is a good source of magnesium not found in food, but surface water, the most common source of supply for drinking water, lacks magnesium. Food processing tends to remove magnesium from foods. Broiling, steaming and boiling remove magnesium into the water or drippings. It has been found that high carbohydrate and high fat diets increase the need for magnesium, as does physical and mental stress. In addition, diuretic medications and insulin further deplete total body magnesium. As the body ages, its ability to absorb magnesium may be impaired. Dieting can also reduce the absorption of already low levels of magnesium intake.

Magnesium is the second most abundant intracellular cation in vertebrates. The magnesium ion is critical cofactor in more than 300 enzymatic reactions involving energy metabolism and protein and nucleic acid synthesis. Accordingly, magnesium is essential for various normal tissue and organ functions. The primary source of magnesium in both humans and animals is from their diets. Most of the studies on the absorption of magnesium in humans and animals suggest that a significant portion is absorbed in the distal intestine, that is, the ileum and colon. The dietary magnesium ion is absorbed in the intestine through both active and passive transport systems. Excessive magnesium is readily excreted through the urine.

Magnesium is a critical element in 325+ biochemical reactions in the human body. Recent research, in France and several other European countries, gives a clue concerning the role of magnesium plays in the transmission of hormones (such as insulin, thyroid, estrogen, testosterone, DHEA, etc.), neurotransmitters (such as dopamine, catecholamines, serotonin, GABA, etc.), and minerals and mineral electrolytes. This research concludes that it is magnesium status that controls cell membrane potential and through this means controls uptake and release of many hormones, nutrients and neurotransmitters. In addition, magnesium modulates the fate of potassium and calcium in the body. If magnesium is insufficient, potassium and calcium will be lost in the urine and calcium will be deposited in the soft tissues (kidneys, arteries, joints, brain, etc.).

Magnesium protects cells from aluminum, mercury, lead, cadmium, beryllium and nickel. Evidence is mounting that low levels of magnesium contribute to the heavy metal deposition in the brain that precedes Parkinson's, multiple sclerosis and Alzheimer's. It is probable that low total body magnesium contributes to heavy metal toxicity in children and is a participant in the etiology of learning disorders.

Magnesium is a mineral that is essential to enzyme reactions in the metabolism of ingested carbohydrates and sometimes has the ability to replace a portion of body calcium. About three-fourths of the mineral found in the body is associated with calcium in the skeleton and tooth dentin formation, with the remainder contained in soft tissues and body fluids. Its specific function is not certain, but studies indicate magnesium probably serves as a catalyst in other physiological activities. Magnesium forms positive ions (charged particles) in solution and is essential to the electrical breakdown of nutrient and other material within the cells. Magnesium is also important to stimulation of muscles and nerves.

Magnesium deficiency is a condition in which an organism fails to receive an adequate supply of magnesium. Poor magnesium status may result in hypomagnesemia or low magnesium levels in the blood. Magnesium deficiencies are noted in chronic kidney disease and other conditions of acidosis (pathological excess of acid), including diabetic coma. Symptoms of deficiency include loss of appetite, muscle weakness, dizziness, distension of the abdomen, convulsive seizures depression and nervousness. Magnesium deficiency (from low dietary intake, metabolic anomalies or excess loss) is clinically associated with: ADD/ADHD, Alzheimer's, angina, anxiety disorders, arrhythmia, arthritis (rheumatoid and osteoarthritis), asthma, autism, autoimmune disorders (all types), cavities, cerebral palsy (in children from magnesium deficient mothers), chronic fatigue syndrome, congestive heart disease, constipation, crooked teeth (narrow jaw—in children from magnesium deficient mothers), depression, diabetes (type 1 and 2), eating disorders (bulimia, anorexia), fibromyalgia, gut disorders (including peptic ulcer, crohn's disease, colitis, food allergy), heart disease (arteriosclerosis, high cholesterol, high triglycerides), heart disease (in infants born to magnesium deficient mothers), high blood pressure, hypoglycemia, impaired athletic performance, infantile seizure (in children from magnesium deficient mothers), insomnia, kidney stones, Lou Gehrig's Disease, migraines (including cluster type), mitral valve prolapse, multiple sclerosis, muscle cramps, muscle weakness (fatigue), myopia (in children from magnesium deficient mothers), obesity (especially obesity associated with high carbohydrate diets), osteoporosis (just adding magnesium reversed bone loss), Parkinson's Disease, PMS (including menstrual pain and irregularities), PPH (primary pulmonary hypertension), Raynaud's, SIDS (sudden infant death syndrome), stroke, syndrome X (insulin resistance), and thyroid disorders (low, high and autoimmune; low magnesium reduces $T_4$). Other conditions are also associated with chronic and acute low magnesium intake and further research is continuing to confirm relationships.

Conversely, an excessive intake of magnesium can cause diarrhea and can interfere with bone formation.

Several studies have reported that increasing calcium in the diet significantly reduces the absorption of magnesium. Calcium intakes above 2.6 grams per day may reduce the uptake and utilization of magnesium by the body and excessive calcium intakes may increase magnesium requirements. The mechanism by which calcium and magnesium interact, however, has not been well defined. Several possible mechanisms have been proposed. These include competition for a common carrier system, a calcium-induced change in membrane permeability to magnesium and a modulation of a specific magnesium carrier by calcium.

The following substances and conditions may reduce total body magnesium and increase magnesium requirements: alcohol (all forms cause significant losses), amphetamines/cocaine, bums (with large surface area), calcium (excessive intake may decrease body magnesium balance), carbohydrates (especially white sugar, high fructose corn syrup, white flour), chronic pain (any cause), coffee (significant losses), cyclosporin (extra magnesium can protect from side-effects), diabetes (magnesium spills with sugar in the urine), diarrhea (any cause), dieting (stress plus lowered intake), diuretics (even potassium sparing diuretics do not spare magnesium), insulin (whether from using insulin or from hyperinsulinemia), over-training (extreme athletic physical conditioning/training), phentermine/fenfluramine, sodas (especially cola type sodas, both diet and regular), sodium (high salt intake), stress (physical and mental—anything that activates a person's fight or flight reaction), surgery and sweat.

The body more efficiently absorbs magnesium (i.e., the bio-uptake is increased) when it is ingested with food and divided into two or more daily doses. Magnesium is available in chelated (bound to) combinations such as alpha-ketogluconate, aspartate, glycinate, lysinate, orotate, taurate and others. Inorganic combinations of magnesium include sulphate, oxide, citrate, carbonate, bicarbonate and chloride. In some cases, inorganic forms of magnesium are not acceptable because they are less soluble and may cause diarrhea and, therefore, may not be effective in correcting a cellular magnesium deficiency.

Soluble magnesium chelates may be the preferred source for daily supplemental use. They include glycinate, lysinate and amino acid chelate. The chelated form of magnesium may assure adequate solubility of magnesium and enhance intestinal uptake. This greatly lessens the possible absorption problems associated with magnesium supplementation and strongly enhances cellular uptake.

One of the major disadvantages of magnesium compositions that are currently available is that they do not control the release of magnesium, but instead immediately release magnesium in the stomach after they are ingested. These products are inefficient because they release magnesium in the upper gastrointestinal tract where it reacts with other substances such as calcium. These reactions reduce the absorption of magnesium. Accordingly, there is a need for a magnesium composition that can provide more efficient absorption of magnesium.

SUMMARY OF THE INVENTION

The present invention is an orally administered pharmaceutical composition which provides controlled release of magnesium and includes a magnesium component, a controlled-release component and an interactive agent component. The interactive agent component includes an agent which interacts with the host to affect bio-uptake of magnesium by the host. If the two components are released simultaneously in the gastrointestinal tract, the absorption of magnesium decreases. Therefore, the interactive agent component is released in the stomach and the release of the magnesium component is released in the intestine. The interactive agent dissolves in the gastric juice of the stomach and substantially all of the interactive agent is released before passage into the intestine of the host. The magnesium component includes magnesium or a magnesium compound and a release-controlling agent which substantially prevents release of magnesium until passage out of the stomach and into the intestine of the host.

The controlled-release component can be an enteric coating having a pH dissolution point of from about 5 to about 8 and preferably from about 6.5 to about 7.2. The enteric coating is applied by contacting the composition with an aqueous suspension or an organic solvent.

In another embodiment, the magnesium is released using a controlled-release matrix system which is capable of releasing the magnesium at a substantially constant rate over a designated time period. Preferably, the controlled-release matrix system is capable of releasing the magnesium at a substantially constant rate over a designated time period of from about 6, 8, 12 and 24 hours. More preferably the designated time period is about 12 hours.

The controlled-release component can be hydroxypropyl methylcellulose ("HPMC"), hydroxypropyl methylcellulose phthalate ("HPMCP"), hydroxyethyl cellulose ("HEC"), hydroxy propyl cellulose ("HPC"), carboxy methyl cellulose ("CMC"), a methacrylic acid copolymer, cellulose acetate phthalate or mixtures thereof. The most preferred controlled-release components are HPMC and HPMCP.

The magnesium component can be a magnesium compound such as magnesium citrate, magnesium gluconate, magnesium oxide, magnesium carbonate, magnesium hydroxide, magnesium sulfate, magnesium phosphate, magnesium aspartate or combinations thereof. The magnesium component can be in the form of a core, a layer or granules.

In a preferred embodiment, the interactive agent component includes calcium or phosphate. When the interactive agent component is calcium, it can be present as calcium carbonate, calcium citrate, calcium propionate, calcium gluconate, calcium sulfate, calcium ascorbate or combinations thereof. The ratio of calcium to magnesium is from 1:5 to 5:1 and preferably from 2:1 to 3:1.

The pharmaceutical composition can be provided in a unit dosage form such as a direct compression tablet, a hard shell capsule, a layered tablet or a dry coated tablet. In one embodiment, the magnesium-containing component can form the core or a layer of a tablet. After the magnesium component is coated, it is combined with the interactive agent component. In another embodiment, the magnesium component and the controlled-release component are contained in a controlled-release matrix. The magnesium component can also be in the form of granules that are pressed into a tablet or placed in a capsule together with the first component.

The present invention also includes a method for delivering magnesium and an interactive agent to a host, i.e., an animal or a human. The method preferably includes delivering magnesium in a form which is not released until it passes through the stomach, while delivering an interactive agent, such as calcium or phosphate, in a form that releases in the stomach. The method includes ingesting a pharmaceutical composition having a magnesium component that includes magnesium or a magnesium compound, a controlled-release component and an interactive agent component. The magnesium compound is preferably magnesium citrate, magnesium gluconate, magnesium oxide, magnesium carbonate, magnesium hydroxide, magnesium sulfate, magnesium phosphate, magnesium aspartate or combinations thereof. The controlled-release component includes either a controlled-release matrix or a pH sensitive enteric polymer coating having a pH dissolution point of from about 6.5 to about 7.2. The interactive agent component includes an agent that interacts with the host to affect bio-uptake of the magnesium. Substantially the entire interactive agent component is released before passage into the intestine of the host and substantially the entire magnesium component is released after passage out of the stomach and into the intestine of the host.

The pharmaceutical composition is preferably in a form suitable for oral administration. This form can be an enterically coated tablet or a tablet having a controlled-release matrix system which is capable of releasing magnesium at a substantially constant rate over a designated time period of about 12 hours. Such tablets can contain about 8 to about 12 wt % HPMC, having an average molecular weight of about 85,000, as the controlled-release component in an amount of, for example, about 10 wt %. The unit dosage is preferably in a form suitable for oral administration. More preferably, the unit dosage is a tablet.

The invention also provides a unit dosage for controlled delivery of magnesium which contains a therapeutically effective amount of a magnesium component dispersed in a controlled-release matrix system containing a controlled-release component capable of providing a release profile which results in a substantially constant release of magnesium over a designated time period.

In another aspect, the invention is a method for the treatment of conditions resulting from magnesium deficiency which involves: administering to a human or animal having a magnesium deficiency a composition which contains a therapeutically effective amount of a magnesium component in enterically coated tablets or particles. The magnesium can also be dispersed in a controlled-release matrix system capable of releasing the magnesium in an amount and at a rate sufficient to maintain effective magnesium absorption over a designated time period. The controlled-release matrix system containing a controlled-release component which contains at least one water-soluble cellulose polymer.

The pharmaceutical composition of the present invention solves the problems caused by the interaction of magnesium with other compounds, especially calcium and phosphate, in the upper gastrointestinal tract. The composition controls the release of magnesium until it reaches the small intestine and colon, where it is most efficiently absorbed by the body.

BRIEF DESCRIPTION OF THE FIGURES

Other objects and many attendant features of this invention will be readily appreciated, as the invention becomes better understood by reference to the following detailed description when considered in connection with the accompanying drawings wherein.

DETAILED DESCRIPTION OF THE INVENTION

Figure 1:
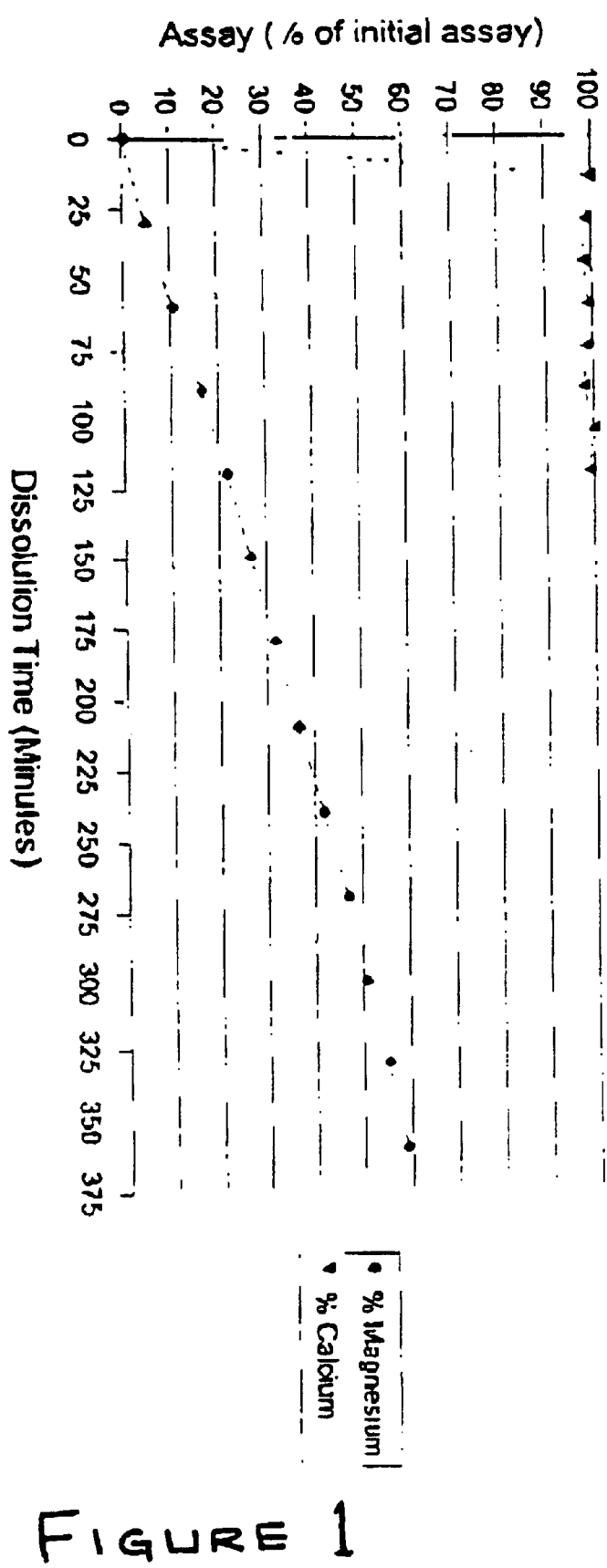
FIG. 1 is a graph showing the rate of dissolution of calcium and magnesium over time.

The present invention is a method and composition for the controlled release of magnesium which provides efficient absorption of magnesium when ingested by humans or animals. The composition includes a magnesium component which does not release until it has passed through the stomach and entered the intestinal tract where magnesium is most efficiently absorbed.

The method and composition of the present invention are designed to be administered orally and can include other components, such as calcium and phosphate, in addition to the magnesium component. In order to prevent the magnesium component from reacting with the other components, the composition has a controlled-release component that protects the magnesium component from the gastric juice in the stomach so that it is not released until the intestinal tract. A particular advantage of the composition is that it controls the release of magnesium until it reaches the lower part of the small intestine where magnesium is most efficiently absorbed. Studies have shown that a significant proportion, if not the bulk of magnesium, is absorbed in the distal intestine, that is, the ileum and colon. The magnesium release is preferably begun in the ileum and is substantially completed by the time the magnesium component has reached the lower part of the colon.

The magnesium component can be essentially magnesium or a magnesium compound such as magnesium citrate, magnesium carbonate, magnesium hydroxide, magnesium gluconate, magnesium oxide, magnesium sulfate, magnesium phosphate or magnesium aspartate. The magnesium component preferably includes a chelated magnesium.

In a preferred embodiment, the composition is made up of: a first component which includes calcium and a second component which includes magnesium and a controlled-release component, preferably an enteric coating or a controlled-release matrix.

The term "lower gastrointestinal tract" is used to refer to the lower part of the small intestine (ileum) and the colon. The term "enteric coating" refers to a coating surrounding the magnesium component of the composition. The composition can be a unit dosage form having a magnesium core coated with an enteric material or the magnesium component can be a layer having an enteric coating. The unit dosage can also have a magnesium component and a controlled-release component contained in a controlled-release matrix. In another embodiment, the magnesium or magnesium component is in the form of granules which have an enteric coating. The solubility of the enteric coating is dependent on the pH in such a manner that it prevents the release of the magnesium in the stomach but permits its release at some stage after passing through the stomach. The term "pH-sensitive enteric polymer" is a polymer which has a solubility that is dependent on the pH. The polymer is preferably insoluble in the gastric juice but dissolves at some stage after the composition passes through the stomach. The term "pH dissolution point" is the pH value in which the pH-sensitive enteric polymer substantially begins to dissolve.

Controlled-release Component

The controlled release of magnesium is provided by the use of a controlled-release component. The controlled-release component is preferably selected from the group consisting of hydroxypropyl methyl cellulose (HPMC), hydroxyethyl cellulose (HEC), hydroxy propyl cellulose (HPC), carboxy methyl cellulose (CMC), and mixtures thereof. The most preferred controlled-release component is HPMC.

The HPMC is preferably a high molecular weight HPMC, having an average molecular weight of at least about 25,000, more preferably at least about 65,000 and most preferably at least about 85,000. The HPMC preferably consists of fine particulates having a particle size such that not less than 80% of the HPMC particles pass through an 80 mesh screen. The HPMC can be included in an amount of from about 4 to about 24 wt %, preferably from about 6 to about 16 wt % and more preferably from about 8 to about 12 wt %, based upon total weight of the composition.

The controlled-release component can include one or more ingredients for controlling the rate at which the magnesium component is made available to the biological system of a host. The controlled-release component can include a delayed release ingredient or a combination of a delayed release ingredient and a sustained release ingredient.

A delayed release ingredient is an ingredient which prevents the active ingredient, i.e., magnesium, from being made available to the host until some time after initial administration. When administration is oral, the delayed release ingredient prevents release of magnesium until the composition has passed through the upper gastrointestinal tract. Examples of delayed release ingredients include, but are not limited to, polymeric or biodegradable coatings or matrices, including water-soluble cellulose polymers.

A sustained release ingredient is an ingredient, or combination of ingredients, which permits release of the magnesium to the host at a certain level over a period of time. Examples of sustained release ingredients include gels, waxes, fats, emulsifiers, combinations of fats and emulsifiers, polymers, starch, water-soluble cellulose polymers, etc., as well as the above in combination with other polymeric or biodegradable coatings or matrices.

The controlled-release component preferably includes at least one water-soluble cellulose polymer. More preferably, the controlled-release component includes at least one water-soluble high molecular weight cellulose polymer. High molecular weight cellulose polymer refers to a cellulose polymer having an average molecular weight of at least about 25,000, preferably at least about 65,000, and more preferably at least about 85,000. The exact molecular weight cellulose polymer used will generally depend upon the desired release profile. For example, polymers having an average molecular weight of about 25,000 are useful in a controlled-release composition having a time release period of up to about 8 hours, while polymers having an average molecular weight of about 85,000 are useful in a controlled-release composition having a time released period of up to about 18 hours. Even higher molecular weight cellulose polymers are contemplated for use in compositions having longer release periods. For example, polymers having an average molecular weight of 180,000 or higher are useful in a controlled-release composition having a time release period of 20 hours or longer.

The controlled-release component preferably consists of a water-soluble cellulose polymer, preferably a high molecular weight cellulose polymer, selected from the group consisting of hydroxypropyl methyl cellulose (HPMC), hydroxyethyl cellulose (HEC), hydroxypropyl cellulose (HPC), carboxy methyl cellulose (CMC), and mixtures thereof. Of these, the most preferred water-soluble cellulose polymer is HPMC. Preferably the HPMC is a high molecular weight HPMC, with the specific molecular weight selected to provide the desired release profile.

Controlled-release Matrix

The magnesium/controlled-release matrix system combination can be administered in the form of a liquid as a suspension or solution, or alternatively in solid form, such as a tablet, pellet, particle, capsule, or soft gel. For example, the form can be polymeric capsules filled with solid particles which can, in turn, be made to release the magnesium according to a known pattern or profile. Such particles can also be made to have more than one release profile so that over an extended time the combined release patterns provide a pre-selected profile.

Preferably, the magnesium/controlled-release matrix system combination is administered in the form of a heterogeneous matrix, such as, for example, a compressed tablet, to control the release of the magnesium either by diffusion, erosion of the matrix or a combination of both.

Another element of the composition is the controlled-release matrix system within which the magnesium is dispersed. The controlled-release matrix system refers to a system containing a continuum of material and a controlled-release component which is present in an amount sufficient to provide a highly predictable pre-selected release profile of the therapeutically active magnesium as a result of normal interaction of the host biosystem on the magnesium/controlled-release matrix system combination. The controlled release component is preferably finely dispersed throughout the matrix. The magnesium is preferably finely dispersed throughout the controlled-release matrix system.

The controlled-release matrix system will preferably provide for a sustained release of magnesium according to a desired release profile through the use of one or more of the release ingredients described above. More preferably, the controlled-release matrix system provides a release profile that releases magnesium at a substantially constant rate over a designated time period.

As the terminology is used herein, "substantially constant rate" refers to maintaining a release rate of the active ingredient, i.e., magnesium, within a desired range over at least about 75% of the designated time period for release, preferably over at least about 80% and more preferably over at least about 90% of the designated time period. The desired range for release is preferably about $4.0 \pm 1.0$ percent of the daily dosage of the active ingredient per hour, more preferably about $4.0 \pm 0.7$ percent per hour and most preferably about $4.0 \pm 0.5$ percent per hour. For example, a 12-hour timed-release magnesium (750 mg of magnesium) tablet, which releases magnesium at a substantially constant rate, would maintain a release rate in the range of about 45 to 75 mg per hour over at least 75 percent of the 12 hour period.

The water-soluble cellulose polymer, e.g., high molecular weight HPMC, is preferably incorporated into the controlled-release matrix system as a fine particulate material having a particle size such that not less than 80% of the particles pass through an 80 mesh screen.

The method of achieving a desired release profile can be varied. For example, the magnesium can be associated physically (which also includes being chemically associated or bound) with the controlled-release component, within the controlled-release matrix system. Alternatively, the active ingredient, i.e., magnesium, can be coated, laminated, encapsulated, etc., with the controlled-release component, within the controlled-release matrix system. Regardless of the method of providing the desired release profile, the present invention contemplates use of a controlled-release component containing one or more of the ingredients, as described above.

A release profile which provides for a substantially constant release rate of magnesium will result in a more consistent magnesium blood serum level over the delivery period. As such, the amount of magnesium delivered can be maximized, while avoiding the side effects attributable to high levels of magnesium.

It has been found that such a release profile can be obtained through the use of a controlled-release matrix tablet, which contains hydroxypropyl methylcellulose ("HPMC") as the primary ingredient of the controlled-release component. The controlled-release component can also contain minor amounts of other materials which can affect the release profile. Examples of such materials include conventional waxes and waxy materials used in pharmaceutical formulations, such as carnuba wax, spermaceti wax, candellila wax, cocoa butter, cetosteryl alcohol, beeswax, partially hydrogenated vegetable oils, ceresin, paraffin, myristyl alcohol, stearyl alcohol, cetyl alcohol and stearic acid. Hydrophilic gums are also contemplated for use, in minor amounts, which can have an effect on the release profile. Examples of hydrophilic gums include acacia, gelatin, tragacanth, veegum, xanthin gum, carboxymethyl cellulose ("CMC"), hydroxy propyl cellulose ("HPC") and hydroxy ethyl cellulose ("HEC").

Preferably, the HPMC in the controlled-release matrix tablet is a high molecular weight HPMC. The specific molecular weight used will typically vary depending upon the desired release profile. For example, a tablet designed to provide a substantially constant release rate over a 12 hour period will preferably contain HPMC having an average molecular weight of at least about 65,000, more preferably about 85,000.

Preferably, the controlled-release matrix tablet will contain about 4 to about 20 wt %, more preferably about 6 to about 16 wt % and most preferably about 8 to about 12 wt % HPMC. The exact amount of HPMC will vary depending upon the molecular weight of the HPMC and the desired release profile. For example, a tablet designed to provide a substantially constant release rate over a 12 hour period, which contains HPMC having a molecular weight of about 85,000, will preferably contain about 8 to about 12 wt %, more preferably about 10%, of the HPMC. The HPMC used in making the controlled-release tablet will preferably be in the form of a fine particulate having a particle size such that not less than 80% of the HPMC passes through an 80 mesh screen.

The amount of magnesium contained in the controlled-release tablet will preferably be an amount sufficient to provide a dosage in the range of about 2 mg to about 12 mg of magnesium per kilogram of body weight per 24-hour period. Preferably, the daily dosage is from about 4 mg to about 10 mg and more preferably about 6 mg per kilogram of body weight. Thus, for a 70 kilogram human or animal, the preferred daily dosage would be in the range from about 140 mg to about 840 mg, more preferably about 280 mg to about 700 mg and most preferably about 420 mg. Preferably, the controlled-release matrix tablet will provide a release profile which releases the magnesium at a substantially constant rate over a designated time period. For example, a 12-hour timed-release tablet will release approximately half of the daily dosage at a substantially constant rate over the 12-hour period.

The Enteric Coating

The enteric coating materials are selected such that the magnesium component will be released at about the time that the composition reaches the small intestine and will continue to be released as the composition passes into and through the colon. The selection of the coating is based upon the pH profile of the small intestine and colon. The pH in the gastrointestinal tract gradually increases as the composition passes through the stomach and into the duodenum from about 1.2 to 3.5 in the stomach to about 4.6 to 5.5 in the duodenal bulb to about 6.5 in the distal portions of the small intestine (ileum). The pH continues to increase until it reaches about 7 to 8 in the colon.

Enteric film-coatings are used to coat the magnesium component of the composition to prevent release of the magnesium in the gastric juice of the stomach, and to delay release until the magnesium component reaches the lower intestine. The enteric coatings are made from non-toxic edible polymers, aqueous dry powder suspensions or cellulose derivatives that are insoluble in the gastric juice of the stomach. The enteric coatings have a pH dissolution point high enough to resist the juices in the stomach but low enough so that the coatings dissolve in the more alkaline intestinal fluid. The pH dissolution point is from about 5.0 pH to 8.0 pH, preferably between 6.5 pH and 7.2 pH. In one embodiment, the coating is a very thin transparent film that includes a cellulose derivative, preferably cellulose acetate phthalate (cellacephate). In another embodiment, the enteric coating is a pH-sensitive enteric polymer. The most preferred coating includes a methacrylate acid copolymer, such as "EUDRAGIT," manufactured by Rohm America, Inc.

An important consideration in selecting a coating is the time it takes for the composition to reach the desired portion of the gastrointestinal tract where the magnesium component is released. When a human ingests the composition, it takes up to three hours for it to pass through the stomach and enter the duodenum (the first part of the small intestine). It then takes from two to twelve hours for the composition to pass through the small intestine and enter the colon, where it can reside for from four to twenty hours.

In order to provide a predictable dissolution time corresponding to the small intestinal transit time of about 3 hours and permit reproducible release of magnesium at the inlet between the small intestine and the colon, or thereafter in the colon, the coating should begin to dissolve within the pH range of the small intestine and continue to dissolve at the pH of the proximal colon. Preferably, the enteric polymer coating material begins to dissolve at a pH range of about 5 to about 6.3. The amount of coating applied is equal in weight to about 4% of the weight of the product that is coated. Single layer enteric coating materials that begin to dissolve at higher pH levels, such as about 7, require less coating thickness for the magnesium component to reach the inlet between the small intestine and the colon, or the colon. However, any coating remaining when the magnesium component reaches the colon will not dissolve in the proximal portions of the colon where the pH is less than 7. As a consequence, the release of the magnesium is delayed until the magnesium component has reached a portion of the colon where the lumenal pH is greater than 7.

A preferred embodiment of the present invention releases the magnesium component in the colon. For this embodiment, the magnesium component has an enteric polymer coating material which begins to dissolve at a pH between about 6.8 to about 7.2 and the layer is completely dissolved less than two hours after the composition is in the colon. The amount and thickness of the enteric coating is such that the release of the magnesium is delayed until the composition has at least reached the inlet between the small intestine and the colon, and preferably reached the colon. The function of the enteric coating is to prevent release of the magnesium as the composition passes through the stomach and a substantial portion of the small intestine so that most of the magnesium is released in the lower part of the small intestine and/or the colon.

Enteric coatings can be applied by coating the tablet with an aqueous solution of a polymeric substance having carboxyl groups in the water-soluble salt form and bringing the thus coated dosage forms into contact with an inorganic acid to convert the polymeric substance into the acid form which is insoluble in water.

Another method of applying enteric coatings is to use an aqueous suspension of a pH sensitive enteric coating polymer such as polyvinylacetate phthalate or cellulose acetate phthalate or a mixture thereof in combination with a plasticizing agent such as triethyl citrate.

Any conventional coating machine such as pan coaters, rotary drum coaters, or fluidizing coaters may be used to apply the coating to the magnesium component. The thickness of the coating film is determined by the kinds of polymeric substances employed, the types and quantities of materials added, the ratio of the mixtures of the polymeric substances and the other materials, the pH values of the internal juices, and the disintegration time in the intestinal juice selected.

Preparation of the Magnesium Composition

The composition can be in the form of a direct compression tablet, a capsule, a bi-layer or multi-layer tablet, a dry coated tablet, an enteric-coated beadlet or an enteric matrix tablet. The composition is designed so that the calcium component is released in the upper gastrointestinal tract and the release of the magnesium component is delayed until the composition reaches the lower gastrointestinal tract. The magnesium component of the composition is preferably in the form of granules, preferably enteric matrix granules coated with enteric film. However, when the composition is in the form of a multi layer tablet, the magnesium component can be an enteric matrix layer coated with an enteric film.

In the manufacture of dry-coated tablets, the magnesium component is formed into a compressed tablet in a first machine and then fed to a second machine where another layer is compressed around it. In this way, magnesium and another component that are normally incompatible may be formulated in the same tablet.

Calcium/Magnesium Composition

In one embodiment of the present invention, the magnesium composition contains a calcium component and a magnesium component. The calcium/magnesium composition is designed to overcome the problems caused by the interaction of calcium and magnesium. When the calcium/magnesium composition is ingested, the calcium component is released into the upper intestinal region immediately, while the release of the magnesium component is delayed. By the time the magnesium composition has passed through the stomach, most of the calcium component has been absorbed and the coated magnesium component is substantially intact.

The uncoated calcium portion of the composition disintegrates rapidly and the individual particles are dispersed in the stomach. The coated portion of the composition is protected from the gastric juice and does not immediately release its contents into the stomach. The enteric coating on the magnesium component does not dissolve until it has reached the more alkaline region of the lower gastrointestinal tract. When the coated magnesium component reaches the lower gastrointestinal tract, the coating dissolves and the magnesium contents are released.

In a preferred embodiment, the first component is essentially calcium or a calcium compound and the second component is essentially magnesium or a magnesium compound, wherein the ratio of calcium to magnesium is from 1:5 to 5:1, preferably from 2:1 to 3:1. The preferred calcium compounds are calcium carbonate, calcium citrate, calcium propionate, calcium gluconate, calcium sulfate or calcium ascorbate. The preferred magnesium compounds are magnesium citrate, magnesium carbonate, magnesium hydroxide, magnesium gluconate, magnesium oxide, magnesium sulfate, magnesium phosphate or magnesium aspartate.

Other combinations which are contemplated include a combination of polymeric material(s) and magnesium which is formed into a sandwich, and which relies on diffusion or erosion to control release of the magnesium. Additionally, heterogeneous dispersions or solutions of magnesium in water-swellable hydrogel matrices are useful in controlling the release of the magnesium by slow surface-to-center swelling of the matrix and subsequent release of the magnesium by a combination of diffusion of the magnesium from the water-swollen part of the matrix and erosion of the water-swollen matrix containing the magnesium.

Other ingredients can be used in accordance with the present invention to improve the tablet. The ingredients can be incorporated during the mixing stage, during the agglomeration stage or after the agglomeration stage. Such ingredients include binders, which contribute to the ease of formation and general quality of the tablet; lubricants, which aid in compressing and compacting the tablet; and flow agents or glidants, which adhere to the cohesive material in order to enhance flow properties by reducing interparticle friction.

Examples of useful binders include calcium sulfate, calcium carbonate, microcrystalline cellulose, starches, lactose, sucrose, mannitol, sorbitol, polyvinylpyrrolidone, methylcellulose, sodium carboxymethylcellulose, ethylcellulose, polyacrylamides, polyvinyloxoazolidone, and polyvinylalcohols. A preferred binder is microcrystalline cellulose, such as Avicel PH-101 sold by FMC Corporation.

Lubricants can include, but are not limited to, the following: magnesium stearate, calcium stearate, zinc stearate, stearic acid, hydrogenated vegetable oils, sterotex, polyoxyethylene, monostearate, talc, polyethyleneglycol, sodium benzoate, sodium lauryl sulfate, magnesium lauryl sulfate and light mineral oil. Of these, the preferred lubricants are magnesium stearate and stearic acid.

Flow agents or glidants which can be used include starch, talc, magnesium and calcium stearate, zinc stearate, dibasic calcium phosphate, magnesium carbonate, magnesium oxide, calcium silicate, silicon dioxide and silica aerogels. A preferred flow agent or glidant is silicon dioxide.

In a preferred embodiment, the controlled-release tablet will be made using an ingredient which acts as both a binder and flow agent (or glidant). A suitable source of such an ingredient is Prosolv SMCC 90 sold by Penwest. Prosolv SMCC 90 contains microcrystalline cellulose and lactose bound to a small percentage of silicon dioxide.

A tablet having sufficient mechanical strength and an acceptable release profile can be produced by mixing a powdered magnesium component with HPMC and suitable binders, lubricants and flow agents and compressing the mixture in a tablet press. A typical compression force used in forming the tablets is in the range of about 45 to about 56 KN, preferably about 50 to about 53 KN, to achieve a tablet having a hardness in the range of about 15 kp to about 30 kp, preferably about 18 kp to about 25 kp.

EXAMPLE 1

The dissolution times for calcium and magnesium were measured by dissolving each in a solution of water having a pH of 7. 331 mg of calcium was placed in a beaker containing the solution an allowed to dissolve. 165 mg of magnesium was then placed in a second beaker and dissolved. The results are listed below in Table 1 and shown graphically in FIG. 1.

TABLE 1

DISSOLUTION RATES OF MAGNESIUM AND CALCIUM
IN A SOLUTION OF WATER AT A pH OF 7

| DISSOLUTION TIME (min) | PERCENT (%) MAGNESIUM | PERCENT (%) CALCIUM |
|---|---|---|
| 0 | 0 | 0 |
| 15 | — | 99.7 |
| 30 | 4.93 | 98.79 |
| 45 | — | 98.19 |
| 60 | 10.61 | 99.09 |
| 75 | — | 96.79 |
| 90 | 16.48 | 97.89 |
| 105 | — | 100 |
| 120 | 21.76 | 99.09 |
| 150 | 26.61 | — |
| 180 | 31.82 | — |
| 210 | 36.67 | — |
| 240 | 41.82 | — |
| 270 | 46.79 | — |
| 300 | 50.67 | — |
| 330 | 55.21 | — |
| 360 | 58.91 | — |

EXAMPLE 2

For the example, 100 mg of magnesium oxide were compressed into a layer HPMC. 250 mg of calcium carbonate were then compressed together with the magnesium oxide layer to form a tablet. The tablet was then placed in a 500 ml beaker containing a dilute solution of citric acid having a pH of 3 for three hours to simulate conditions in the stomach. After fifteen minutes, the calcium carbonate layer had dissolved but the magnesium oxide layer was substantially intact after three hours. The magnesium oxide layer was then removed from the citric acid solution and placed in a beaker containing water having a pH of 7. After several minutes the magnesium oxide layer began to dissolve and was totally dissolved after one and a half hours.

EXAMPLE 3

For this example, 100 mg of magnesium citrate granules were coated with an enteric coating containing HPMC. The coated magnesium citrate granules were then mixed with 250 mg of calcium sulfate and placed in a gelatin capsule that dissolved at a pH of about 3.

Thus, while there have been described the preferred embodiments of the present invention, those skilled in the art will realize that other embodiments can be made without departing from the spirit of the invention, and it is intended to include all such further modifications and changes as come within the true scope of the claims set forth herein.

We claim:

1. A unit dosage form tablet or capsule composition for oral administration comprising
   a) an enteric coated magnesium component having an active ingredient consisting essentially of one or more magnesium compounds, wherein said enteric coating is a polymeric release-controlling agent which substantially prevents release of said one or more magnesium compounds until passage out of the stomach and into the intestine of the host, and wherein said release-controlling agent has a pH dissolution point of from about 5 to about 8; and
   b) an uncoated calcium component having an active ingredient consisting essentially of one or more calcium compounds;

wherein substantially all of said calcium component is released before passage into said intestine of said host, and wherein the ratio of said calcium component to said magnesium component is from 1:5 to 5:1.

2. A unit dosage form tablet or capsule composition according to claim 1, wherein said release-controlling agent has a pH dissolution point of from about 6.5 to about 7.2.

3. A unit dosage form tablet or capsule composition according to claim 1, wherein the ratio of said calcium component to said magnesium component is from 2:1 to 3:1.

4. A unit dosage form tablet or capsule composition according to claim 1, wherein said enteric coating is applied by contacting said magnesium component with an aqueous suspension or an organic solvent.

5. A unit dosage form tablet or capsule composition according to claim 1, wherein said enteric coating is selected from the group consisting of hydroxypropyl methylcellulose phthalate ("HPMCP") and a methacrylic acid copolymer.

6. A unit dosage form tablet or capsule composition according to claim 4, wherein said aqueous suspension is polyvinylacetate phthalate or cellulose acetate phthalate or a mixture thereof in combination with a plasticizing agent.

7. A unit dosage form tablet or capsule composition according to claim 1, wherein said magnesium component of said composition is one of a core, a layer or granules.

8. A unit dosage form tablet or capsule composition according to claim 7, wherein said one or more magnesium compounds is selected from the group consisting of magnesium citrate, magnesium gluconate, magnesium oxide, magnesium carbonate, magnesium hydroxide, magnesium sulfate, magnesium phosphate, magnesium aspartate and combinations thereof.

9. A unit dosage form tablet or capsule composition according to claim 1, wherein said composition is selected from the group consisting of a direct compression tablet, a hard shell capsule, a layered tablet or a dry coated tablet.

10. A unit dosage form tablet or capsule composition according to claim 1, wherein said one or more calcium compounds is calcium carbonate, calcium citrate, calcium propionate, calcium gluconate, calcium sulfate, calcium ascorbate or combinations thereof.

11. A unit dosage form tablet or capsule composition for oral administration comprising:
    a) an enteric coated magnesium component having an active ingredient consisting essentially of one or more magnesium compounds selected from the group consisting of magnesium citrate, magnesium gluconate, magnesium oxide, magnesium carbonate, magnesium hydroxide, magnesium sulfate, magnesium phosphate, magnesium aspartate and combinations thereof, wherein said magnesium component has a pH sensitive enteric polymer coating having a pH dissolution point of from about 5 to about 8; and
    b) an uncoated calcium component having an active ingredient consisting essentially of one or more calcium compounds selected from the group consisting of calcium carbonate, calcium citrate, calcium propionate, calcium gluconate, calcium sulfate, calcium ascorbate and combinations thereof, wherein the ratio of said calcium component to said magnesium component is from 1:5 to 5:1.

12. A method for delivering to a host magnesium and calcium, said method comprising:
    ingesting a unit dosage form tablet or capsule composition comprising:
    a) an enteric coated magnesium component having an active ingredient consisting essentially of one or more magnesium compounds selected from the group consisting of magnesium citrate, magnesium gluconate, magnesium oxide, magnesium carbonate, magnesium hydroxide, magnesium sulfate, magnesium phosphate, magnesium aspartate and combinations thereof, wherein said enteric coating is a pH sensitive enteric polymer coating having a pH dissolution point of from about 5 to about 8; and b) an uncoated calcium component having an active ingredient consisting essentially of one or more calcium compounds;

wherein substantially all of said calcium component is released before passage into said intestine of said host and substantially all of said magnesium component is released after passage out of the stomach and into the intestine of the host, and wherein the ratio of said calcium component to said magnesium component is from 1:5 to 5:1.

13. A method for delivering to a host magnesium and calcium according to claim 12, wherein the ratio of said calcium component to said magnesium component is from 2:1 to 3:1.

14. A method for delivering to a host magnesium and calcium according to claim 12, wherein said one or more calcium compounds is calcium carbonate, calcium citrate, calcium propionate, calcium gluconate, calcium sulfate, calcium ascorbate or combinations thereof.

* * * * *

UNITED STATES PATENT AND TRADEMARK OFFICE
CERTIFICATE OF CORRECTION

PATENT NO. : 6,887,492 B2
DATED : May 3, 2005
INVENTOR(S) : Kay et al.

It is certified that error appears in the above-identified patent and that said Letters Patent is hereby corrected as shown below:

<u>Column 3,</u>
Line 20, now reads "cocaine, bums (with large surface area), calcium (excessive" should read -- cocaine, burns (with large surface area), calcium (excessive --.

Signed and Sealed this

Eleventh Day of October, 2005

JON W. DUDAS
*Director of the United States Patent and Trademark Office*